United States Patent [19]

Drews

[11] Patent Number: 4,817,599

[45] Date of Patent: Apr. 4, 1989

[54] TO AND FRO WASHING SYSTEM AND METHOD

[76] Inventor: Robert C. Drews, 211 N. Meramec Ave., Clayton, Mo. 63105

[21] Appl. No.: 139,730

[22] Filed: Dec. 30, 1987

[51] Int. Cl.$^4$ .............................................. A61B 17/00
[52] U.S. Cl. .................................. 128/303 R; 604/27; 604/73; 604/151
[58] Field of Search ...................... 604/151, 31, 36, 73, 604/27; 128/303 R, DIG. 24 A, 305

[56] References Cited

U.S. PATENT DOCUMENTS

| 4,275,726 | 6/1981 | Schael | 604/31 |
| 4,314,560 | 2/1982 | Helfgott et al. | 604/73 |
| 4,424,055 | 1/1984 | Herman | 604/36 |
| 4,482,345 | 11/1984 | Chow et al. | 604/151 |

OTHER PUBLICATIONS

Stedman's Medical Dictionary, 24th Edition, p. 1064.
Ophthalmic Surgery, "A New Infusion-Aspiration System for Extracapsular Cataract Surgery", Aug., 1987, vol. 18, No. 8, pp. 618-620.

*Primary Examiner*—C. Fred Rosenbaum
*Assistant Examiner*—Gene B. Kartchner
*Attorney, Agent, or Firm*—Hugh D. Jaeger

[57] ABSTRACT

An autoclavable to and fro washing system and method of operation for use in extracapsular cataract surgery with and without infusion. A hand-held, motorized pump unit includes a reversing peristaltic pump for moving an IV solution back and forth through a hollow probe tip keeping the anterior chamber of the eye filled with fluid and safe from collapse, while the cortex of the cataract is emulsified using to and fro washing through the hollow probe tip and then flushed from the eye by the IV solution. Infusion and to and fro washing flow and pressure rates are proportionally varied by a switch on the hand held pump unit, or alternatively by a foot switch. An alternative embodiment includes a smaller and lighter hand piece, including a peristaltic pump and motor located remote from a hand piece and probe tip.

4 Claims, 5 Drawing Sheets

TO AND FRO WASHING SYSTEM AND METHOD

BACKGROUND OF THE INVENTION

1. Field of the Invention

The present invention pertains to and fro washing system and method, and more particularly, pertains to a hand-held to and fro washing system for use in removal of the cortex and/or nucleus in extracapsular cataract surgery.

2. Description of the Prior Art

Extracapsular surgery currently is performed using manual or console-driven systems. Modern extracapsular cataract surgery uses an infusion system to keep the anterior chamber of the eye filled with fluid and safe from collapse while the cortex of the cataract is removed by aspiration.

Manual systems generate suction by a syringe connected directly, or indirectly via flexible tubing to the cannula. Such have the advantage of excellent response time as far as changing the aspiration pressure, but require bi-manual operation and often considerable and prolonged, forceful pulling on the syringe plunger. This can make it difficult to direct the aspiration tip with the required microscopic precision, occasionally leading to surgical complications. This type of manual action is tedious and fatiguing and sometimes leads to microscopic positioning errors or inadvertent small movements creating subsequent surgical complications.

For these reasons, most surgeons find manual aspiration techniques unsatisfactory, and use various console operated systems. These contain pumping devices for the aspiration of cortex with control provided through a foot pedal. In order to avoid collapsing the eye while pumping material out of it, such are also provided with an infusion system to replace the material removed from the eye by intravenous fluids.

Console-operated systems are expensive, and the annual cost of disposables can far exceed the initial investment. The operating area can become cluttered with cords and tubing. Because of the complexity of these systems, maintenance is required and dysfunction may occur during surgery. There is usually a delay between a command via the foot pedal and, its accomplishment at the tip of the to and fro washing cannula. If, for example, the surgeon needs to stop aspirating instantly and releases the foot control switch, the long lengths of flexible tubing may allow to and fro washing to continue in the anterior chamber, even though the pump has stopped, until the tubing reexpands to its resting state. Even if the system is "vented" to atmospheric pressure, as is true in most consoles, anterior chamber fluid will continue to flow into the tubing until the pressure in the anterior chamber becomes zero.

A previous unit used a syringe with a motor simply to drive a piston in a syringe; there were two problems with that method of operation. When the syringe was filled, the surgeon had to stop whatever he was doing, remove the to and fro washing tip from the patient's eye and sit there for a minute or so and empty the syringe before he could proceed. Secondly, as manufactured, the unit was not autoclavable and had to be gas sterilized. For many surgeons throughout the world, gas sterilization, such as ETO, is not available so the unit could not be used by them. Furthermore, having to be gas sterilized, it was impossible to resterilize it inbetween cases, so that if a surgeon was doing several cases in a day, he would have to own several units which made the unit much more expensive.

If the unit were autoclavable, a surgeon could own one or two units and do all of his cases during the day.

In a later unit, the syringe was replaced by a peristaltic pump. The unit was autoclavable, and a surgeon could own one or two units and do all of his cases during the day.

The purpose of the present system importantly is to provide automated to and fro motion of the fluid from a cannula in the anterior chamber of the eye, such that lens material (especially cortex, but sometimes also soft nuclear material) is gently and safely emulsified by being drawn in (in small quantities) and expelled from the opening of the cannula, and can be washed from the eye (or aspirated). In so doing it allows very safe removal of the material from the eye with very precise positioning of the cannula tip and minimal risk of damage to the lens capsule and other delicate ocular tissues.

The controls for this system provide three positions, as currently embodied: OFF, INFUSION (to deepen the anterior chamber of the eye and wash out emulsified lens material), and TO-AND-FRO (to emulsify the lens material). The latter position can be extended by providing adjustable volumes of the to-and-fro motion either with a rheostat or (for example, in a foot pedal) with an accelerator-like motion of the pedal.

SUMMARY OF THE INVENTION

The general purpose of the present invention is to provide a to and fro washing action so that the cortex and/or nucleus lens material is washed in and out of the cannula. This emulsifies the cortex very gently in a subsonic phakoemulsification. The emulsified cortex is then washed away by infusing an excess amount of fluid into the eye in a washing cycle, or in the alternative, by having a double cannula with constant infusion. It can also be aspirated if desired.

According to one embodiment of the present invention, there is provided an infusion and to and fro washing system including a motorized pump unit, an IV supply and a combination power supply and foot switch. A motorized pump unit includes a reversible peristaltic pump mounted at one end. IV fluid can be pumped from an IV source bag by the peristaltic pump, and is delivered under variable pressure to a hollow probe tip or cannula for infusion. To and fro washing action is provided by reversing the peristaltic pump motor back and forth through an electrical control circuit. The electrical foot or like switch is used to control these functions and is provided with an "off position", an infusion position, and a variable to and fro motion portion.

One significant aspect and feature of the present invention is an infusion and to and fro washing with a peristaltic pump mounted on a pump unit.

Another significant aspect and feature of the present invention is an infusion and to and fro washing using short and/or rigid tubing to provide quick pressure response times with minimal hysteresis.

A further significant aspect and feature of the present invention is a hand-operated proportional rocker switch which can be mounted on the motorized pump unit or used separately.

Still another significant aspect and feature of the present invention is a proportional external electrical foot or like switch.

Another significant aspect and feature of the present invention is a separable peristaltic pump housing.

Other significant aspects and features of the present invention include emulsification and washout of cortex and/or nucleus which is safer in many cases than aspiration. The apparatus is automated to accomplish this type of removal of lens material.

Having thus described embodiments of the present invention, it is the principal object hereof to provide an autoclavable, hand-held infusion and to and fro washing system and method of operation for use in extracapsular cataract surgery in emulsifying the lens material of cortex and/or nucleus.

BRIEF DESCRIPTION OF THE DRAWINGS

Other objects of the present invention and many of the attendant advantages of the present invention will be readily appreciated as the same become better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
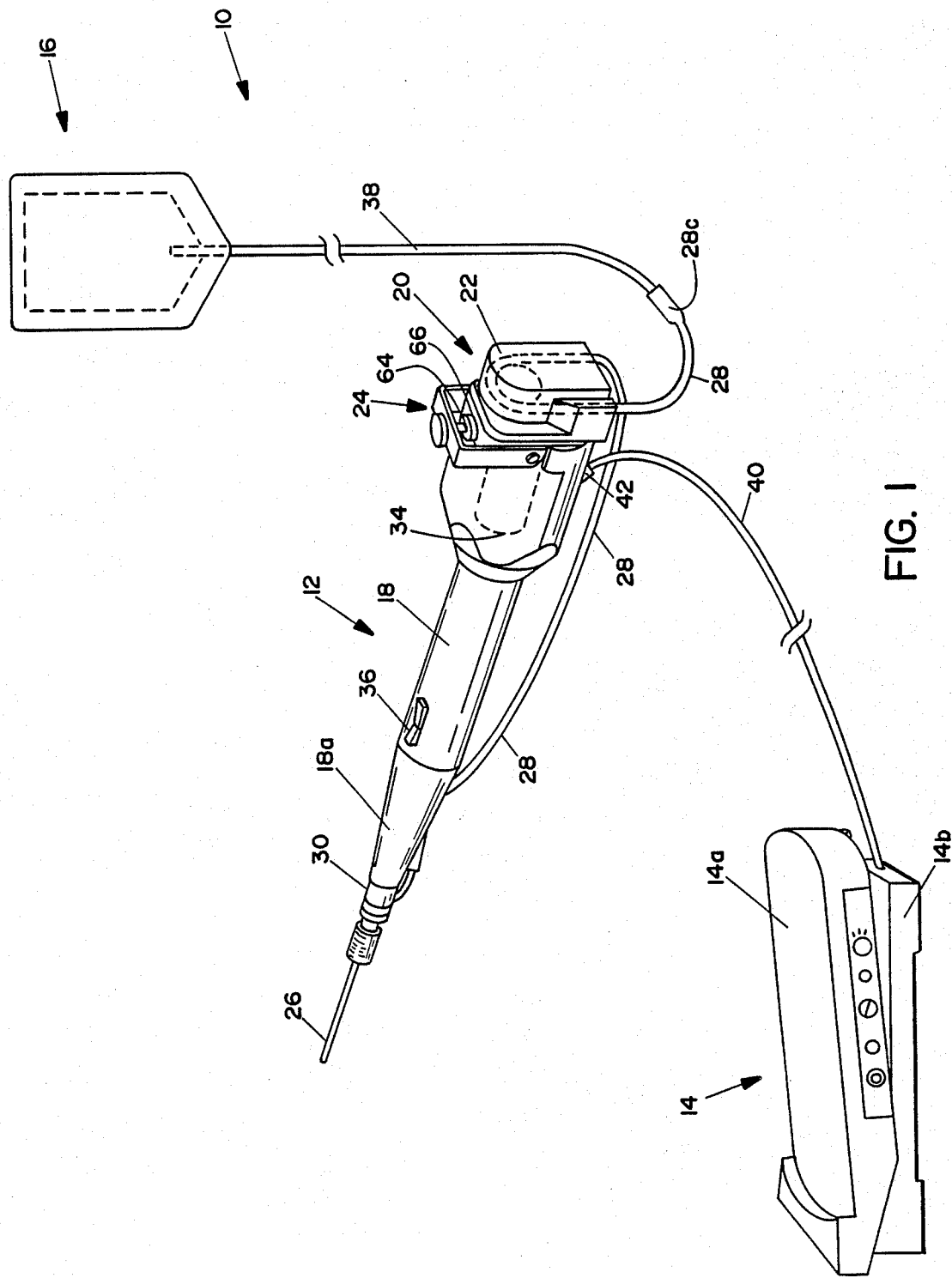
FIG. 1 illustrates an extracapsular infusion and to and fro washing system.

FIG. 1 illustrates an extracapsular infusion and to and fro washing system 10 including a hand-held motorized pump unit 12, a combination power supply and an optional foot switch 14, and an IV bag 16. The main components of the hand-held motorized pump unit 12 include a body member 18; a tapered body member portion 18a; a peristaltic pump 20 with a removable housing 22 and a housing clamp 24 on one end of the body member 18; a hollow probe tip or cannula 26; a tube 28 between the peristaltic pump and the cannula mounting fitting 30; a reversible motor 34 which drives the peristaltic pump 20; and a proportional rocker control switch 36 mounted in the body member 18 accommodating either left or right handed operation. A tube 38 connects the IV bag 16 to the peristaltic pump tube end 28a of tube 28. Tube 28 passes through and is an integral part of the peristaltic pump 20, to the cannula mounting fitting 30 over which the hollow cannula tip 26 is frictionally engaged. The proportional rocker control switch 36 provides for finger tip directional control of the reversible motor 34. The rocker control switch 36 is a proportional rocker switch, where the speed of the reversible motor 34 is proportional to the amount of pressure applied to either end of the switch to provide for variable speed operation of the reversible motor 34. Thus, the peristaltic pump 20 rotates in two directions either for infusion of an IV medium from the IV bag 16, or for to and fro washing action of the cortex and/or nucleus at different rates. A foot switch 14a, part of the power supply and foot switch 14, provides an optional way to control pump and motor direction, and provides the same function as the proportional rocker control switch 36 to provide for either infusion or to and fro washing of the cortex and/or nucleus. The foot switch could be the preferred operational switch in lieu of the rocker switch in the housing. A battery power supply 14b is provided for powering the reversible motor 34. An electrical control cable 40 connects between the battery power supply 14b and the reversible motor 34 via a strain relief member 42.

Figure 2:
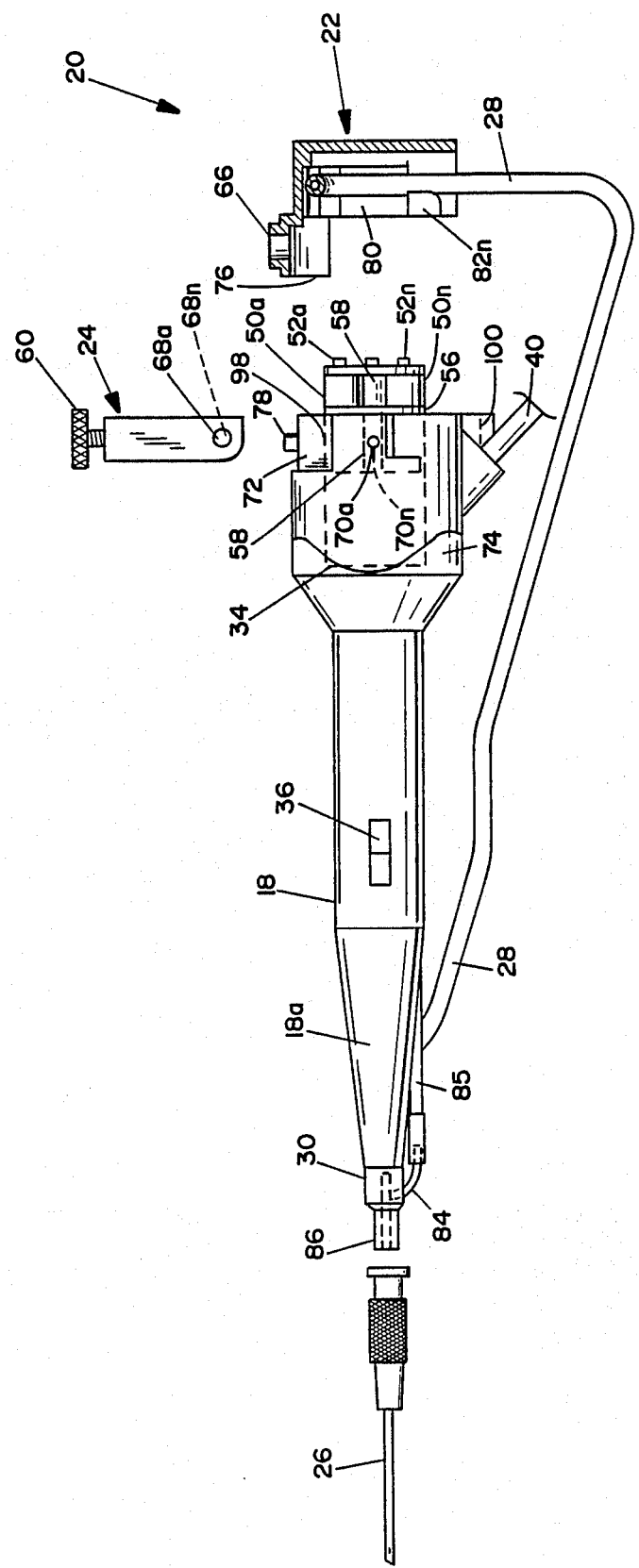
FIG. 2 illustrates an exploded side view in partial cross section of the infusion and to and fro washing system.
Figure 3:
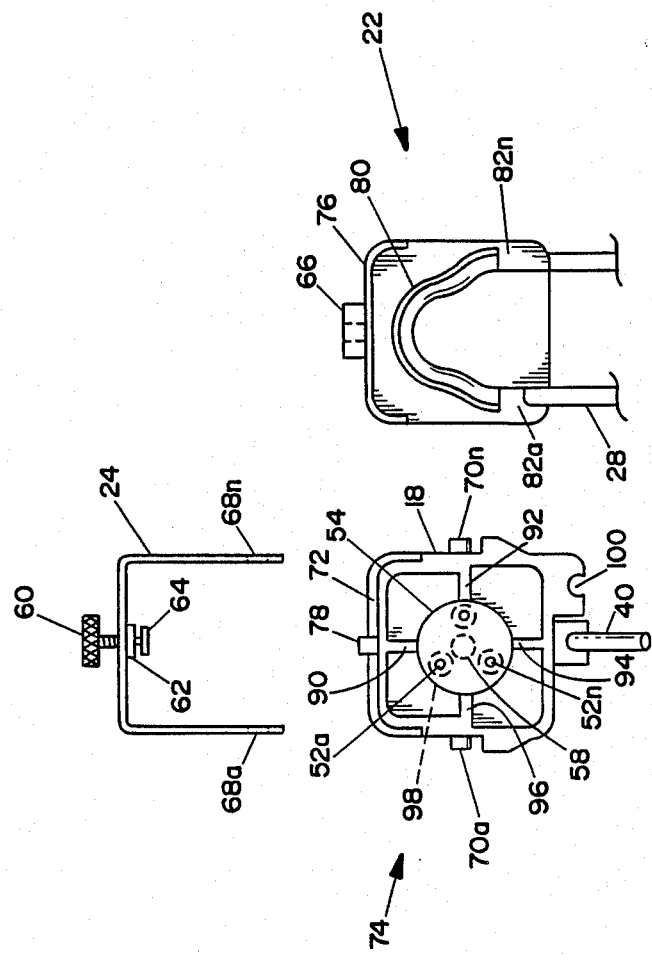
FIG. 3 illustrates an exploded end view of the peristaltic pump with the removable housing removed and rotated.

FIG. 2 illustrates an exploded side view in partial cross section where all numerals correspond to those elements previously described. Shown in particular is the peristaltic pump 20. The reversible motor 34 turns a plurality of rollers 50a-50n located on pins 52a-52n between circular plates 54 and 56 via shaft 58. The removable housing 22, including the tube 28, engages over the rollers 50a and 50n and their associated components, and is held in place by the housing clamp 24, which includes a knurled adjustment screw 60 engaged in a threaded member 62, an integral part of the housing clamp 24. A circular foot pad area 64 on the bottom of the knurled adjustment screw 60 presses downwardly on a cylindrical hollow protrusion 66 on the removable housing 22, as also illustrated in FIG. Holes 68a-68n in the lower portions of the housing clamp 24 fit over cylindrical protrusions 70a-70n to secure the housing clamp 24 to the body member 18 and motor casing 74 in the area of the peristaltic pump 20. A channel-like recessed area 72, along the upper edge of a motor casing 74, part of the body member 18, accepts a corresponding channel-shaped upper edge member 76 of the removable housing 22. These channel members are also illustrated in FIG. 3. A solid cylindrical member 78 extends upwardly from the upper surface of the channel-like recessed area 72 to engage within the cylindrical hollow protrusion 66 on the channel-like upper edge member 76 of the removable housing 22. After engagement of the removable housing 22 over the motor casing 74, in particular, after the engagement of the channel-like upper edge member 76 over the channel like recessed area 72, and after the engagement of the cylindrical hollow protrusion 66 over the solid cylindrical member 78, the knurled adjustment screw 60 is tightened forcing the circular foot pad area 64 of FIG. 3 against the cylindrical hollow protrusion 66; thus, forcing the removable housing 22 and tube 28 downwardly and into position against rollers 50a-50n of the peristaltic pump 20. The tube 28 is held in position in a semicircular cavity 80 in the removable housing 22 by cylindrical tube slots 82a and 82n as illustrated in FIG. 3. The cannula mounting fitting 30 includes an angled tube 84 for accommodation of the flexible tube 28 and a hollow shaft 86 for accommodation of the hollow cannula tip 26. Another tube slot 85 is located on the underside of the tapered body member portion 18a for securement of the tube 28 to the tapered body member portion 18a.

FIG. 3 illustrates an exploded end view of the peristaltic pump 20 where the removable housing 22 has been removed and rotated 180° to expose the semicircular cavity 80 of the removable housing 22 and where all numerals correspond to those elements previously described. The end view of the motor casing 74 includes struts 90-96 which support a cylindrical housing 98 for the centering of the shaft 58. A flexible tube slot 100 positions on the lower edge of the motor casing 74 for securement of the tube 28 to the motor casing 74.

Figure 4:
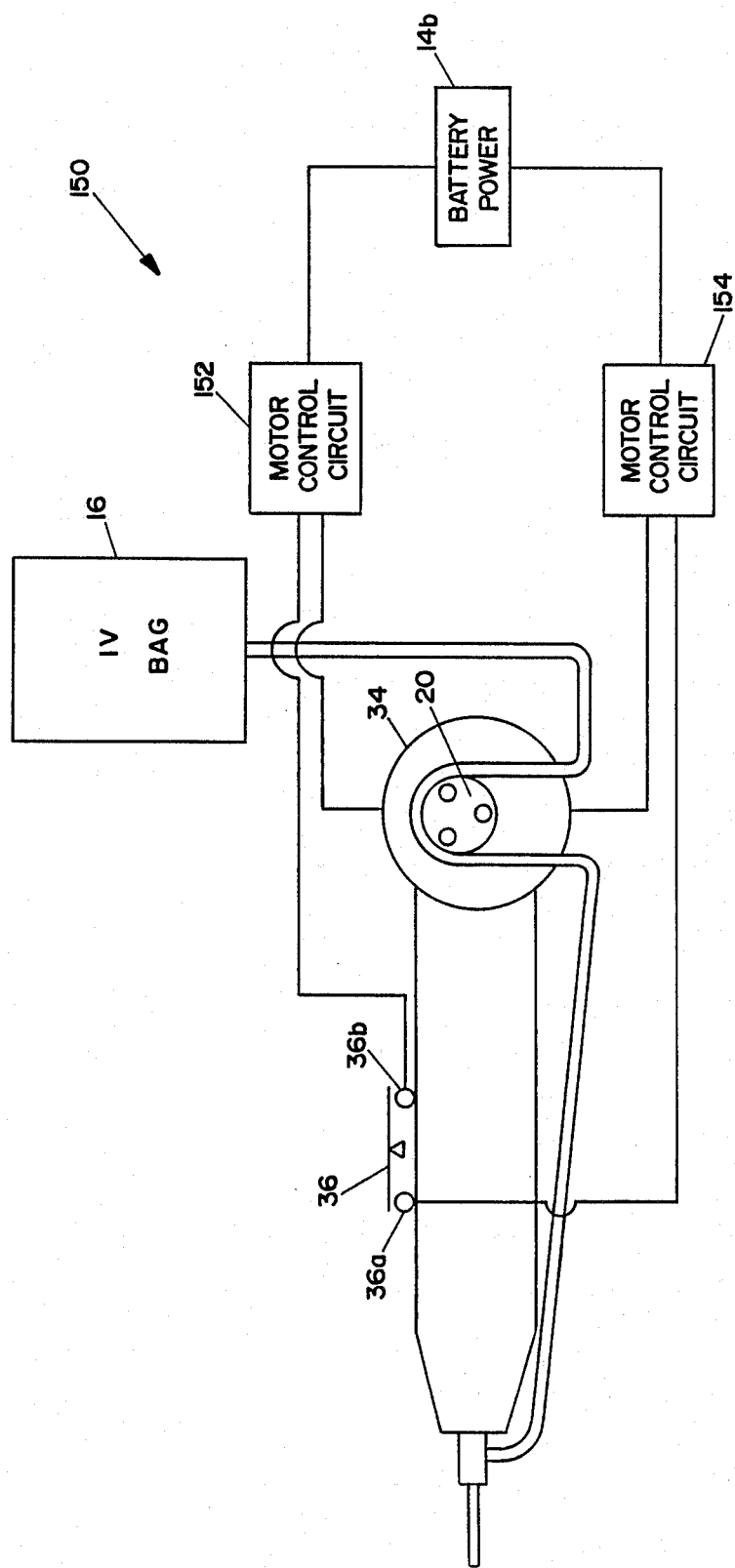
FIG. 4 illustrates an electrical block diagram of the system.

FIG. 4 illustrates an electrical schematic block diagram 150 of the system including the fluid flow path.

Battery power 14b energizes the motor 34 through variable speed motor control circuits 152 and 154 as switched by switch 36. The switch 36 includes a forward to and fro emulsifying position 36a and an infusion position 36b. The degree of pressure applied to the switch in either direction correspondingly controls the speed of the motor through the motor control circuit. In the emulsifying switch position 36a, the motor control circuit 154 controls the motor forward and reverse in a variable rotation providing a to and fro washing action to emulsify the cortex and/or nucleus. The motor control circuits can include analog or digital control for increasing the speed of rotation of the motor dependent upon the degree that the foot or rocker switch is depressed. Position 36b provides for fluid infusion for washing away of emulsified cortex and/or nucleus from the eye.

MODE OF OPERATION

The system 10 provides a to and fro washing action to emulsify the cortex and/or nucleus which is then washed away by infusing an excess amount of fluid into the eye in a washing cycle.

The tubing is connected to balanced salt solution and all air removed from the tubing and cannula. The cannula is introduced into the eye while the control switch/pedal is in the INFUSION position to maintain the anterior chamber depth and prevent any eye collapse. The cannula tip is directed under control with the operating microscope to lens material to be removed, positioning the (end or side) port of the cannula against or in the material. The switch is now shifted/depressed to the TO-AND-FRO position and—with gentle automated motion—the lens material is emulsified. The stroke volume can be increased or decreased as the surgeon judges optimum. Returning to the INFUSION position, this emulsified material is washed from the eye. The cycle is then repeated in another area where more lens material needs to be removed. When sufficient (all) lens material has been removed, the cannula is withdrawn from the eye and the switch/pedal allowed to return to the OFF position.

DESCRIPTION OF AN ALTERNATIVE EMBODIMENT

Figure 5:
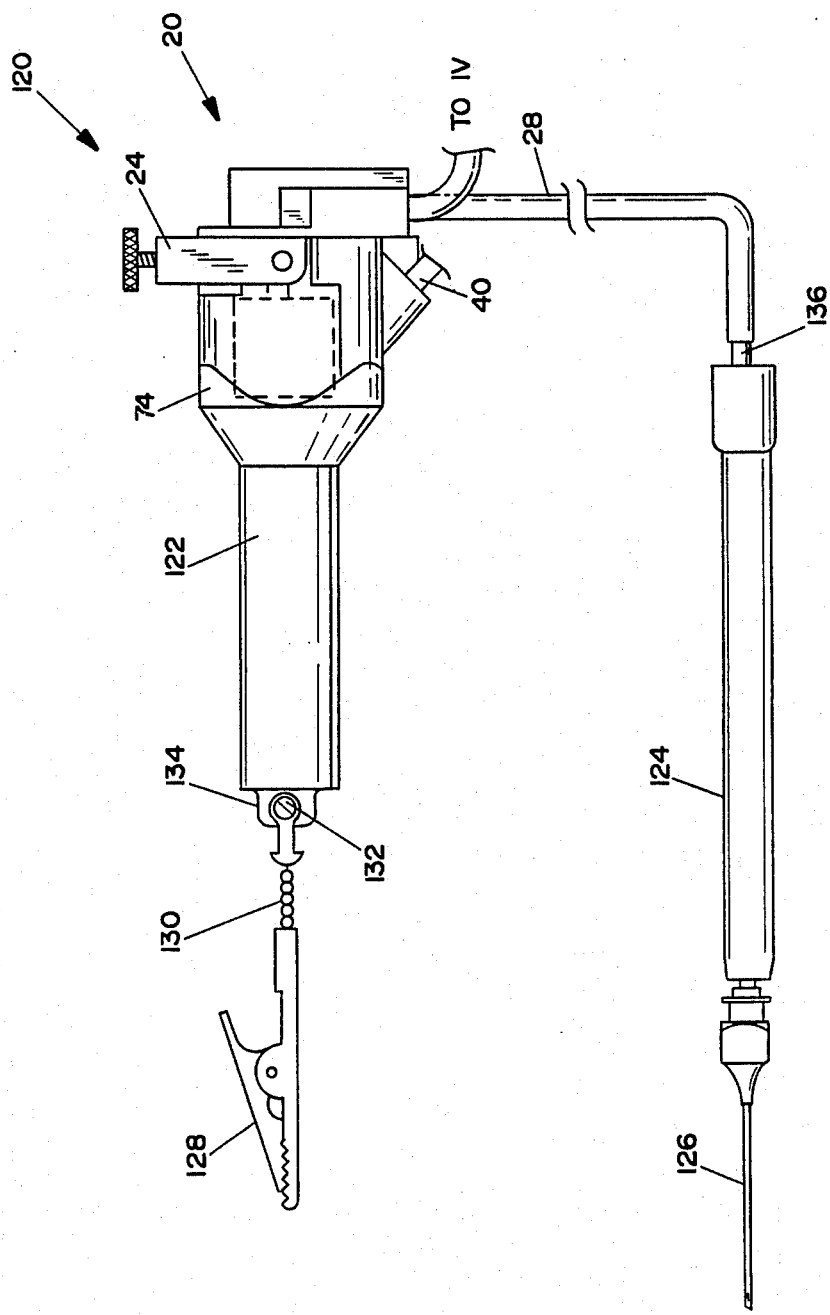
FIG. 5 illustrates an alternative embodiment of an infusion aspirator.

FIG. 5 illustrates an alternative embodiment of an infusion aspirator 120 where the motorized pump unit body 122 includes the same peristaltic pump 20 and associated components, a light weight hand piece 124, and probe tip 126 which operates remotely from the motor pump unit body 122. A clip 128, for hanging the motor pump unit body 122 to any convenient fixture in the operating environment, such as surgery drape, secures to one end of the motor pump unit body 122 with a small chain 130 and a screw 132 passing through a mounting tab 134 on the end of the motor pump unit body 122. The tube 28 for peristaltic pump 20 attaches to a port 136 on the light weight hand piece 124 to supply to and fro washing or infusion at the probe tip 126 at the opposite end of the light weight hand piece 124. The power supply foot switch 14 is used to operate and power the infusion aspirator 120.

Various modifications can be made to the present invention without departing from the apparent scope thereof.

For example, it is foreseen that hard nuclei may be attacked by this instrument or a modification of it. Likewise, other pump systems can be used, such as for example an oscillating piston, and so on.

I claim:

1. System for emulsifying cortex and/or nucleus in the capsular bag comprising:
    a. a housing including a body member;
    b. cannula means supported within said housing and including a configured hole at a tube end and a fluid port at a body member end;
    c. motor means including peristaltic pump therein connected to said fluid port;
    d. power means for said motor means; and,
    e. motor control means connected between said motor means and said power means for reciprocally powering said motor means in a to and fro rotating action, whereby said to and fro rotating action provides a to and fro washing action that emulsifies the cortex and/or nucleus lens material in and out of said hole in said cannula.

2. Process of infusion and to and fro washing for extracapsular cataract surgery comprising the steps
    a. initially stripping cortex in a capsular bag of an eye;
    b. washing cortex and/or nucleus in and out of a cannula in a to and fro washing action thereby emulsifying said cortex and/or nucleus; and,
    c. eliminating said emulsified cortex and/or nucleus from said capsular bag and said eye.

3. Process of claim 2 wherein said eliminating step comprises the step of infusing an excess amount of fluid into said eye in a washing cycle.

4. Process of claim 2 wherein said emulsifying action is subsonic phakoemulsification.

* * * * *